「(12) United States Patent
Salerno

(10) Patent No.: US 10,435,446 B2
(45) Date of Patent: *Oct. 8, 2019

(54) CELL PENETRATING PROTEIN ADAPTOR MOLECULES AND THEIR APPLICATION IN RESEARCH AND MEDICINE

(71) Applicant: Kennesaw State University Research and Service Foundation Inc., Kennesaw, GA (US)

(72) Inventor: John C. Salerno, Acworth, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/545,637

(22) Filed: Jun. 3, 2015

(65) Prior Publication Data

US 2016/0355561 A1    Dec. 8, 2016

(51) Int. Cl.
| | | |
|---|---|---|
| *C07K 14/46* | (2006.01) |
| *A61K 38/17* | (2006.01) |
| *C07K 14/47* | (2006.01) |
| *A61K 38/44* | (2006.01) |

(52) U.S. Cl.
CPC .......... *C07K 14/4728* (2013.01); *A61K 38/44* (2013.01); *C07K 2319/10* (2013.01); *C12N 2740/16322* (2013.01); *C12Y 114/13039* (2013.01)

(58) Field of Classification Search
CPC .......... A61K 47/48315; A61K 49/0056; A61K 49/0058; A61K 38/44; C07K 14/4728
See application file for complete search history.

(56) References Cited

U.S. PATENT DOCUMENTS

| | | | |
|---|---|---|---|
| 6,316,003 B1 * | 11/2001 | Frankel | A61K 47/48238 424/192.1 |
| 6,589,503 B1 * | 7/2003 | Piwnica-Worms | A61K 47/48338 424/1.11 |
| 7,034,109 B2 | 4/2006 | Bonny | |
| 7,538,091 B2 | 5/2009 | Bonny | |
| 7,569,674 B2 | 8/2009 | Kohler et al. | |
| 7,662,178 B2 | 2/2010 | Marks et al. | |
| 7,727,958 B2 | 6/2010 | Li | |
| 7,754,678 B2 | 7/2010 | Guo et al. | |
| 7,927,580 B2 | 4/2011 | Cohen | |
| 8,067,532 B2 | 11/2011 | MacLean | |
| 8,080,517 B2 | 12/2011 | Bonny | |
| 8,183,339 B1 | 5/2012 | Bonny | |
| 8,236,924 B2 | 8/2012 | Bonny | |
| 8,273,867 B2 | 9/2012 | Dowdy et al. | |
| 8,278,413 B2 | 10/2012 | Bonny | |
| 8,524,673 B2 | 9/2013 | Li | |
| 8,569,447 B2 | 10/2013 | Bonny | |
| 8,748,395 B2 | 6/2014 | Bonny | |
| 2002/0013003 A1 * | 1/2002 | Wagner | G01N 33/52 436/518 |
| 2003/0161809 A1 * | 8/2003 | Houston | A61K 38/1709 424/85.2 |
| 2006/0141549 A1 | 6/2006 | Mahajan et al. | |
| 2011/0027300 A1 | 2/2011 | Kamil et al. | |
| 2016/0304562 A1 * | 10/2016 | Salerno | A61K 47/48315 |

FOREIGN PATENT DOCUMENTS

| | | |
|---|---|---|
| EP | 1544305 A1 | 6/2005 |
| EP | 1605893 A2 | 12/2005 |
| EP | 1964853 A1 | 9/2008 |
| WO | 2003077931 A1 | 9/2003 |
| WO | 2004030610 | 4/2004 |
| WO | 2004064780 | 8/2004 |
| WO | 2005059129 A2 | 6/2005 |
| WO | 2010/010112 | 1/2010 |
| WO | 2015/134920 | 9/2015 |

OTHER PUBLICATIONS

Soughayer et al., (Biochem. 2004;43:8528-8540).*
UniProt Q13555 (KCC2G_Human) (Apr. 12, 2005, v3; last accessed Apr. 11, 2017; 19 pages).*
Copolovici et al., (ACS Nano. 2014: 8(3). 1972-1994). (Year: 2014).*
Dominici et al., (Vaccine., May 16, 2003. 21(17-18): 2073-81). (Year: 2003).*
Abdiche, Y., Malashock, D., Pinkerton, A., & Pons, J., Determining kinetics and affinities of protein interactions using a parallel real-time label-free biosensor, the Octet, Analytical Biochemistry 377, 209-217, (2008).
Capes-Davis, A., Theodosopoulos, G., Atkin, I., Drexler, H.G., Kohara, A., MacLeod, R.A., Masters, J.R., Nakamura, Y., Reid, Y.A., Reddel, R.R., Freshney, R.I., (2010) Check your cultures! A list of cross-contaminated or misidentified cell lines. Int. J. Cancer, 127, 1-8.
Cardozo, A.K. et al., Cell-permeable peptides induce dose- and length-dependent cytotoxic effects, Biochimica et Biophysica Acta 1768 (2007) pp. 2222-2234.

(Continued)

*Primary Examiner* — Christine J Saoud
(74) *Attorney, Agent, or Firm* — Smith, Gambrell & Russell LLP

(57) ABSTRACT

Coupling proteins that make strong protein-protein interactions equipped with cell penetrating peptides (CPPs) provide a convenient and powerful method to perturb cell interiors; there are many potential payloads and a broad palette of selectively membrane permeable probes. In a preferred embodiment, the coupling protein will be calmodulin or a related calcium binding protein. In a preferred embodiment, the CPP will be TAT or another CPP. In a preferred embodiment, the coupling protein will release its payload after targeting to an interior compartment. Cargo proteins can be purified by affinity methods using the same tag that allows binding by the adaptor, enabling an integrated approach with 'gains in both function and safety. Access to cell interior compartments has potential applications in research, diagnostics, and therapeutics.

12 Claims, 7 Drawing Sheets
(3 of 7 Drawing Sheet(s) Filed in Color)
Specification includes a Sequence Listing.

(56) References Cited

OTHER PUBLICATIONS

Chaloin, L. et al., Design of carrier peptide-oligonucleotide conjugates with rapid membrane translocation and nuclear localization properties. Biochem. Biophys. Res. Commun. 243, 601-608 (1998).
DeFilippis, R.A., Goodwin, E.C., Wu, L. and Dimaio, D., (2003) Endogenous human papillomavirus eand e& proteins differentially regulate proliferation, senescence, and apoptosis in HeLa cervical carcinoma cells. J. Virology, 77 (1551-1563).
El-Andaloussi, T. Holm, U. Langel, Cell-penetrating peptides: mechanism and applications, Curr. Pharma. Design 11 (2005) 3597-3611.
Elliott, G., and O'Hare, P., Intercellular trafficking and protein delivery by a herpesvirus structural protein. Cell 88, 223-233 (1997).
Erazo-Oliveras, A., Muthukrishnan, N., Baker, R., Wang, T.-Y., & Pellois, J., Improving the Endosomal Escape of Cell-Penetrating Peptides and Their Cargos: Strategies and Challenges, Pharmaceuticals 5, pp. 1177-1209, (2012).
Fonseca, S. B., Pereira, M. P. & Kelley, S. O. Recent advances in the use of cell-penetrating peptides for medical and biological applications. Adv. Drug Deliv. Rev. 61, 953-964 (2009).
Gautam, A. et al., CPPsite: a curated database of cell penetrating peptides. Database (Oxford) vol. Article ID bas015, (2012).
Geller, D.A., Lowenstein, C.J., Shapiro, R.A., Nussler, A.K., Di Silvio, M., Wang, S.C., Nakayama, D.K., Simmons, R.L., Snyder, S.H., Billiar, T.R., (Apr. 1993). Molecular cloning and expression of inducible nitric oxide synthase from human hepatocytes. Proc. Natl. Acad. Sci. U.S.A. 90 (8): 3491-5.
Glogau, R. et al., J. Drugs Dermatol. 11, 38-45 (2012).
Green, M. & Loewenstein, P. M., Autonomous functional domains of chemically synthesized human immunodeficiency virus Tat trans-activator protein. Cell 55, 1179-1188 (1988).
Hirose, H. et al., Transient Focal Membrane Deformation Induced by Arginine-rich Peptides Leads to Their Direct Penetration into Cells, Molecular Therapy, vol. 20, No. 5, pp. 984-993, (2012).
Houdusse, A., and Cohen, C., Target recognition by the calmodulin superfamily: Implications from light chain binding to the regulatory domain of scallop myosin Proc. Natl. Acad. Sci. USA vol. 92, pp. 10644-10647, Nov. 1995.
Hudmon, Andy, Schulman, Howard, (2002). Neuronal Ca2+/Calmodulin-Dependent Protein Kinase II: The Role of Structure and Autoregulation in Cellular Function. Annual Review of Biochemistry 71: 473-510.
Johnson, R. M., Harrison, S. D., & Maclean, D., Therapeutic applications of cell-penetrating peptides. Methods Mol. Biol. 683, 535-551 (2011).
Krebs, Joachim, Heizmann, Claus W., Calcium-binding proteins and the EF-hand principle, pp. 51-93 in Calcium A Matter of Life or Death (Joachim Krebs and Marek Michalak Editors) vol. 41 (2007) Elsevier, Gottigen, Germany.
Krossa, S., Schmitt, A. D., Hattermann, K., Fritsch, J., Scheidig, A. J., Mehdorn, H. M., & Held-Feindt, J., Down regulation of Akirin-2 increases chemosensitivity in human glioblastomas more efficiently than Twist-1, Oncotarget vol. 6, No. 25, (2015).
Lonn, P. & Dowdy, S.F. Expert Opin. Drug Deliv. 26, 1-10 (2015).
Lundberg, M., Wikstrom, S. & Johansson, M., Cell Surface Adherence and Endocytosis of Protein Transduction Domains, Molecular Therapy,.vol. 8, No. 1, pp. 143-150, (2003).
Macville M, Schröck E, Padilla-Nash H, Keck C, Ghadimi BM, Zimonjic D, Popescu N, Ried T., (1999) Comprehensive and definitive molecular cytogenetic characterization of HeLa cells by spectral karyotyping. Cancer Research, 59, 141-150.
Magzoub M., Kilk K., Eriksson L. E., Langel U. and Graslund A., (2001) Interaction and structure induction of cell-penetrating peptides in the presence of phospholipid vesicles. Biochim. Biophys. Acta 1512: 77-89 S.
Mantovani, F., and Banks, L., 2001. The human papillomavirus E6 protein and its contribution to malignant progression. Oncogene 20: pp. 7874-7887.
Mathisen et al., J Biol Chem. 1999; 274(44):31571-6.

McMurry, J.L. et al., Rate, affinity and calcium dependence of nitric oxide synthase isoform binding to the primary physiological regulator calmodulin, FEBS Journal, vol. 278, pp. 4943-4954, (2011).
McMurry, J.L. et al., Weak Interactions between *Salmonella enterica* FlhB and other Flagellar Export Apparatus Proteins Govern Type III Secretion Dynamics, PLOS One, DOI: 10.1371/journal.pone.0134884 (2015).
Mitchell, D. J., Kim, D. T., Steinman, L., Fathman, C. G. & Rothbard, J. B., Polyarginine enters cells more efficiently than other polycationic homopolymers. J. Pept. Res. 56, pp. 318-325, (2000).
Morris, M. C., Vidal, P., Chaloin, L., Heitz, F. & Divita, G., A new peptide vector for efficient delivery of oligonucleotides into mammalian cells. Nucleic Acids Res. 25, 2730-2736 (1997).
Nowak, S. J., & Baylies, M. K., (2012). Akirin: a context-dependent link between transcription and chromatin remodeling. Bioarchitecture, 2(6), 209-213.
Palm-Apergi, C., Lonn, P. & Dowdy, S.F., Do Cell-Penetrating Peptides Actually "Penetrate" Cellular Membranes?, Molecular Therapy, vol. 20, No. 4, pp. 695-697, (2012).
Rickhag, Mattias, Owens, William A., Winkler, Marie-Therese, Norgaard-Strandfelt, Kristine, Rathje, Mette, Sorensen, Gunnar, Andresen, Bjorn, Madsen, Kenneth L., Nygaard-Jorgensen, Trine, Wortwein, Gitta, Woldbye, David P. D., Sitte, Harald, Daws, Lynette C., and Gether, Ulrik, Membrane-permeable C-terminal Dopamine Transporter Peptides Attenuate Amphetamine-evoked Dopamine Release J. Biol. Chem. 2013 288: 27534-27544.
Säälik, P., Elmquist, A, Hansen, M., Padari, K., Saar, K., Viht, K., Langel, U., Pooga, M., Protein cargo delivery properties of cell-penetrating peptides. A comparative study. Bioconjug Chem. Nov.-Dec. 2004; 15(6):1246-53.
Sebbage, V., Bioscience Horizons 2, 64-72 (2009).
Stratton, M.M., Chao, L.H., Schulman, H., Kuriyan, J., Structural studies on the regulation of Ca2+/calmodulin dependent protein kinase II. Curr Opin Struct Biol. Apr. 2013; 23 (2):292-301.
Sultana, A. & Lee, J.E. Curr. Protoc. Protein Sci. 79, 19.25.11-19.25-26 (2015).
Trabulo, S., Cardoso, A. L., Mano, M. & De Lima, M. C. P. Cell-penetrating peptides-Mechanisms of cellular uptake and generation of delivery systems. Pharmaceuticals 3, 961-993 (2010).
Usui, T., Okada, M., Hara, Y., Yamawaki, H., Vascular effects of novel calmodulin-related proteins that mediate development of hypertension Folia Pharmacologica Japonica vol. 141 (2013) No. 2 p. 85-89.
Wadia JS, Stan RV, Dowdy SF: Transducible TAT-HA fusogenic peptide enhances escape of TAT-fusion proteins after lipid raft macropinocytosis. Nat Med 2004, 10:310-315.
Wagstaff, Kylie M.; Jans, David A., Protein Transduction: Cell Penetrating Peptides and Their Therapeutic Applications; Current Medicinal Chemistry, vol. 13, No. 12, May 2006, pp. 1371-1387(17).
Weigel, Aubrey V., Tamkun, Michael M., and Krapf, Diego, PNAS Plus: Quantifying the dynamic interactions between a clathrin-coated pit and cargo molecules PNAS 2013 110 (48) E4591-E4600; published ahead of print Nov. 11, 2013.
Zur Hausen, H., (1999) Immortalization of human cells and their malignant conversion by high risk human papillomavirus genotypes. Semin. Cancer Biol. 9: 405-411.
Salerno et al., Novel cell penetrating peptide-adaptors effect intracellular delivery and endosomal escape of protein cargos; Journal of Cell Science; vol. 129, No. 5, pp. 893-897; advanced online publication Jan. 22, 2016, Retrieved from the internet: <URL: http://jcs.biologists.org/content/joces/early/2016/01/21/jcs.182113.full.pdf.
Eguchi et al., Efficient siRNA delivery by novel PTD-DRBD fusion proteins; Cell Cycle. (Feb. 1, 2010) vol. 9, No. 3, pp. 424-425.
Dooley et al., Imaging Dynamic Redox Changes in Mammalian Cells with Green Fluorescent Protein Indicators; Journal of Biological Chemistry (May 21, 2004) vol. 279, No. 21, pp. 22284-22293.
Reissmann, Cell penetration: scope and limitations by the application of cell-penetrating peptides; Journal of Peptide Science (Oct. 2014) vol. 20, No. 10, pp. 760-784.

(56) References Cited

OTHER PUBLICATIONS

International Search Report and Written Opinion in International Patent Application No. PCT/US2017/016189 (Jun. 5, 2017, 13 pages).
Montrose, Kristopher et al.; Xentry, a new class of cell-penetrating peptide uniquely equipped for delivery of drugs, Scientific Reports 3, Article No. 1661 (Apr. 16, 2013, 7 pages).
International Patent Application No. PCT/US2017/016189; Int'l Preliminary Report on Patentability; dated Aug. 16, 2018; 8 pages.

* cited by examiner

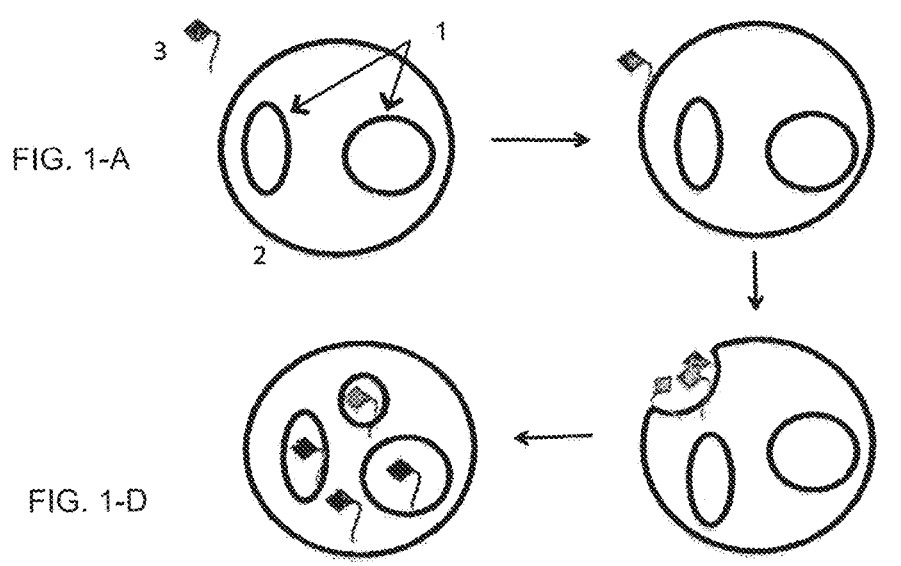

FIG. 2-A
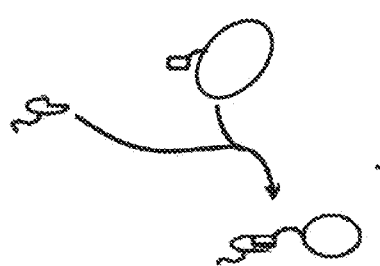
FIG. 2-B
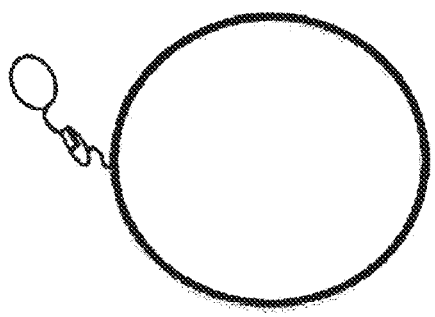
FIG. 2-D
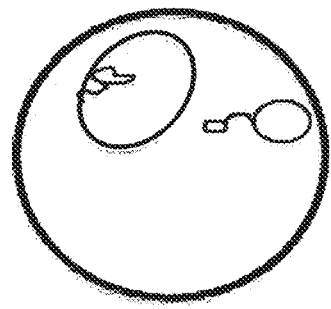
FIG. 2-C
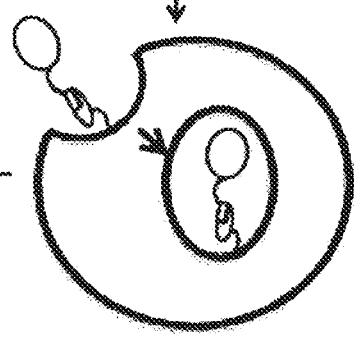

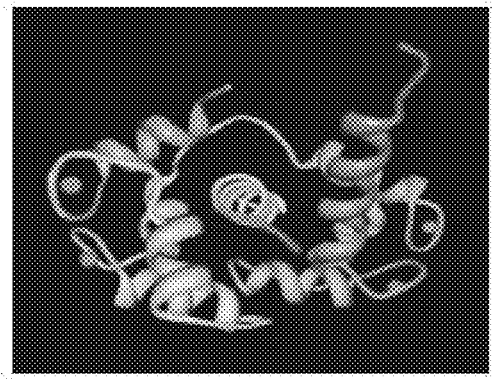 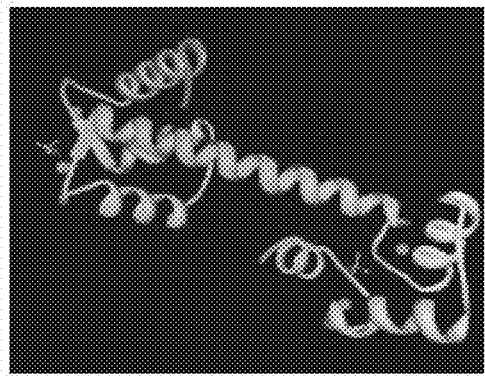
FIG. 4-A          FIG. 4-B

FIG. 5

```
                                                                        *:  :   :
1       ------------------------------------------------MADQLTEEQIAEF    13   CALM_
1       ---------------------------------------------MTDQQAEARSYLSEEMIAEF 20   TNNC2
1       -------------------------------MASGFKKPSAASTGQKRKVAPKPELTEDQKQEV  33   CETN1
1       ---------------------------------------------------MAGELTPEEEAQY  13   CALL5
1       MAAEHLLPGPPPSLADFRLEAGGKGTERGSGS----SKPTGSSRGPRMAKFLSQDQINEY       56   CALL4

: .*.    *  :  *  *  .:*  ,.::  *          ::   :.   :*  *  :.*   **.
14      KEAFSLFDKDGDGTITTKELGTVMRSLGQNPTEAELQDMINEVDADGNGTIDFPEFLTMM       73   CALM_
21      KAAFDMFDADGGGDISVKELGTVMRMLGQTPTKEELDAIIEEVDEDGSGTIDFEEFLVMM       80   TNNC2
34      REAFDLFDVDGSGTIDAKELKVAMRALGFEPRKEEMKKMISEVDREGTGKISFNDFLAVM       93   CETN1
14      KKAFSAVDTDGNGTINAQELGAALKATGKNLSEAQLRKLISEVDSDGDGEISFQEFLTAA       73   CALL5
57      KECFSLYDKQQRGKIKATDLMVAMRCLGASPTPGEVQRHLQTHGIDGNGELDFSTFLTIM      116   CALL4

::::    .:    .*  :     :*        *: :  .:*::  ::   :.*
74      ARKMKDT---DSEEEIREAFRVFDKDGNGYISAAELRHVMTNLGEKLTDEEVDEMIREAD      130   CALM_
81      VRQMKEDAKGKSEEELAECFRIFDRNADGYIDPEELAEIFRASGEHVTDEEIESLMKDGD      140   TNNC2
94      TQKMSEK---DTKEEILKAFRLFDDDETGKISFKNLKRVANELGENLTDEELQEMIDEAD      150   CETN1
74      KKAR------AGLEDLQVAFRAFDQDGDGHITVDELRRAMAGLGQPLPQEELDAMIREAD      127   CALL5
117     HMQIKQE----DFKKEILLAMLMVDKEKKGYVMASDLRSKLTSLGERLTHKEVDDLFREAD     173   CALL4

131     IDGDGQVNYEEFVQMMTAK----  149   P62158    CALM_HUMAN
141     KNNDGRIDFDEFLKMMEGVQ---  160   P02585    TNNC2_HUMAN
151     RDCDGEVNEEEFLRIMKKTSLY-  172   Q12798    CETN1_HUMAN
128     VDQDGRVNYEEFARMLAQE----  146   Q9NZT1    CALL5_HUMAN
174     IEPNGKVKYDEFIBKITLPGRDY  196   Q96GE6    CALL4_HUMAN
```

FIG. 6

HM YGRKKRRQRRR           NOT1              MADQLTEEQIAEFKE
AFSLFDKDGDGTITTKELGTVMRSLGQNPTEAELQDMINEVD
ADGNGTIDFPEFLTMMARKMKDTDSEEEIREAFRVFDKDGNG
YISAAELRHVtTNLGEKLTDEEVDEMIREADIDGDGQVNYEEF
VQMMTAK Stop Codon BamH1 site Kpn1 site FIG. 7-A
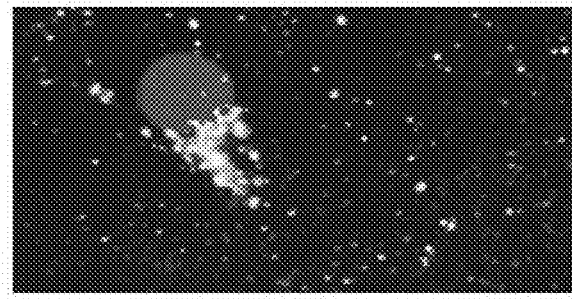
FIG. 7-B
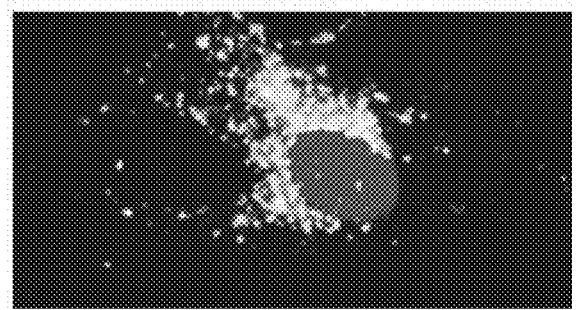

SEQUENCE LISTING

<160> NUMBER OF SEQ ID NOS: 23

<210> SEQ ID NO 1
<211> LENGTH: 149
<212> TYPE: PRT
<213> ORGANISM: Homo sapiens

<400> SEQUENCE: 1

Met Ala Asp Gln Leu Thr Glu Glu Gln Ile Ala Glu Phe Lys Glu Ala
1               5                   10                  15

Phe Ser Leu Phe Asp Lys Asp Gly Asp Gly Thr Ile Thr Thr Lys Glu
            20                  25                  30

Leu Gly Thr Val Met Arg Ser Leu Gly Gln Asn Pro Thr Glu Ala Glu
        35                  40                  45

Leu Gln Asp Met Ile Asn Glu Val Asp Ala Asp Gly Asn Gly Thr Ile
50                  55                  60

Asp Phe Pro Glu Phe Leu Thr Met Met Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
        115                 120                 125

Ala Asp Ile Asp Gly Asp Gly Gln Val Asn Tyr Glu Glu Phe Val Gln
130                 135                 140

Met Met Thr Ala Lys
145

<210> SEQ ID NO 2
<211> LENGTH: 160
<212> TYPE: PRT
<213> ORGANISM: Homo sapiens

<400> SEQUENCE: 2

Met Thr Asp Gln Gln Ala Glu Ala Arg Ser Tyr Leu Ser Glu Glu Met
1               5                   10                  15

Ile Ala Glu Phe Lys Ala Ala Phe Thr Met Phe Asp Ala Asp Gly Gly
            20                  25                  30

Gly Asp Ile Ser Val Met Glu Leu Gly Thr Val Met Arg Met Leu Gly
        35                  40                  45

Gln Thr Pro Thr Lys Glu Glu Leu Asp Ala Ile Ile Glu Glu Val Asp
50                  55                  60

Glu Asp Gly Ser Gly Thr Ile Asp Phe Glu Glu Phe Leu Val Met Met
65                  70                  75                  80

Val Arg Gln Met Lys Glu Asp Ala Arg Gly Lys Ser Glu Glu Glu Leu
                85                  90                  95

Ala Glu Cys Phe Arg Ile Phe Asp Arg Asn Ala Asp Gly Tyr Ile Asp
            100                 105                 110

Pro Glu Glu Leu Ala Glu Ile Phe Arg Ala Ser Gly Glu His Val Thr
        115                 120                 125

Asp Glu Glu Ile Glu Ser Leu Met Lys Asp Gly Asp Lys Asn Asn Asp
130                 135                 140

Gly Arg Ile Asp Phe Asp Glu Phe Leu Lys Met Met Glu Gly Val Gln
145                 150                 155                 160

<210> SEQ ID NO 3
<211> LENGTH: 172
<212> TYPE: PRT
<213> ORGANISM: Homo sapiens

<400> SEQUENCE: 3

```
Met Ala Ser Gly Phe Lys Lys Pro Ser Ala Ser Thr Gly Gln Lys
1               5                   10                  15

Arg Lys Val Ala Pro Lys Pro Glu Leu Thr Glu Asp Gln Lys Gln Glu
            20                  25                  30

Val Arg Glu Ala Phe Asp Leu Phe Asp Val Asp Gly Ser Gly Thr Ile
        35                  40                  45

Asp Ala Lys Glu Leu Lys Val Ala Met Arg Ala Leu Gly Phe Glu Pro
    50                  55                  60

Arg Lys Glu Glu Met Lys Lys Met Ile Ser Glu Val Asp Arg Glu Gly
65                  70                  75                  80

Thr Gly Lys Ile Ser Phe Asn Asp Phe Leu Ala Val Met Thr Gln Lys
                85                  90                  95

Met Ser Glu Lys Asp Thr Lys Glu Glu Ile Leu Lys Ala Phe Arg Leu
            100                 105                 110

Phe Asp Asp Asp Glu Thr Gly Lys Ile Ser Phe Lys Asn Leu Lys Arg
        115                 120                 125

Val Ala Asn Glu Leu Gly Glu Asn Leu Thr Asp Glu Glu Leu Gln Glu
    130                 135                 140

Met Ile Asp Glu Ala Asp Arg Asp Gly Asp Gly Glu Val Asn Glu Glu
145                 150                 155                 160

Glu Phe Leu Arg Ile Met Lys Lys Thr Ser Leu Tyr
                165                 170

<210> SEQ ID NO 4
<211> LENGTH: 196
<212> TYPE: PRT
<213> ORGANISM: Homo sapiens

<400> SEQUENCE: 4

Met Ala Ala Glu His Leu Leu Pro Gly Pro Pro Ser Leu Ala Asp
1               5                   10                  15

Phe Arg Leu Glu Ala Gly Gly Lys Gly Thr Glu Arg Gly Ser Gly Ser
            20                  25                  30

Ser Lys Pro Thr Gly Ser Ser Arg Gly Pro Arg Met Ala Lys Phe Leu
        35                  40                  45

Ser Gln Asp Gln Ile Asn Glu Tyr Lys Glu Cys Phe Ser Leu Tyr Asp
    50                  55                  60

Lys Gln Gln Arg Gly Lys Ile Lys Ala Thr Asp Leu Met Val Ala Met
65                  70                  75                  80

Arg Cys Leu Gly Ala Ser Pro Thr Pro Gly Glu Val Gln Arg His Leu
                85                  90                  95

Gln Thr His Gly Ile Asp Gly Asn Gly Glu Leu Asp Phe Ser Thr Phe
            100                 105                 110

Leu Thr Ile Met His Met Gln Ile Lys Gln Glu Asp Pro Lys Lys Glu
        115                 120                 125

Ile Leu Leu Ala Met Leu Met Val Asp Lys Lys Lys Gly Tyr Val
    130                 135                 140

Met Ala Ser Asp Leu Arg Ser Lys Leu Thr Ser Leu Gly Glu Lys Leu
145                 150                 155                 160

Thr His Lys Glu Val Asp Leu Phe Arg Glu Ala Asp Ile Glu Pro
                165                 170                 175

Asn Gly Lys Val Lys Tyr Asp Glu Phe Ile His Lys Ile Thr Leu Pro
            180                 185                 190

Gly Arg Asp Tyr
            195
```

<210> SEQ ID NO 5
<211> LENGTH: 146
<212> TYPE: PRT
<213> ORGANISM: Homo sapiens

<400> SEQUENCE: 5

```
Met Ala Gly Glu Leu Thr Pro Glu Glu Ala Gln Tyr Lys Lys Ala
1               5                   10                  15

Phe Ser Ala Val Asp Thr Asp Gly Asn Gly Thr Ile Asn Ala Gln Glu
                20                  25                  30

Leu Gly Ala Ala Leu Lys Ala Thr Gly Lys Asn Leu Ser Glu Ala Gln
            35                  40                  45

Leu Arg Lys Leu Ile Ser Glu Val Asp Ser Asp Gly Asp Gly Glu Ile
50                  55                  60

Ser Phe Gln Glu Phe Leu Thr Ala Ala Lys Lys Ala Arg Ala Gly Leu
65                  70                  75                  80

Glu Asp Leu Gln Val Ala Phe Arg Ala Phe Asp Gln Asp Gly Asp Gly
                85                  90                  95

His Ile Thr Val Asp Glu Leu Arg Arg Ala Met Ala Gly Leu Gly Gln
            100                 105                 110

Pro Leu Pro Gln Glu Glu Leu Asp Ala Met Ile Arg Glu Ala Asp Val
        115                 120                 125

Asp Gln Asp Gly Arg Val Asn Tyr Glu Glu Phe Ala Arg Met Leu Ala
130                 135                 140

Gln Glu
145
```

<210> SEQ ID NO 6
<211> LENGTH: 180
<212> TYPE: PRT
<213> ORGANISM: Artificial Sequence
<220> FEATURE:
<223> OTHER INFORMATION: /note="Description of Artificial Sequence: Synthetic peptide"

<400> SEQUENCE: 6

```
His Met Tyr Gly Arg Lys Lys Arg Arg Gln Arg Arg Asn Thr Met
1               5                   10                  15

Ala Asp Gln Leu Thr Glu Glu Gln Ile Ala Glu Phe Lys Glu Ala Phe
                20                  25                  30

Ser Leu Phe Asp Lys Asp Gly Asp Gly Thr Ile Thr Thr Lys Glu Leu
            35                  40                  45

Gly Thr Val Met Arg Ser Leu Gly Gln Asn Pro Thr Glu Ala Glu Leu
50                  55                  60

Gln Asp Met Ile Asn Glu Val Asp Ala Asp Gly Asn Gly Thr Ile Asp
65                  70                  75                  80

Phe Pro Glu Phe Leu Thr Met Met Ala Arg Lys Met Lys Asp Thr Asp
                85                  90                  95

Ser Glu Glu Glu Ile Arg Glu Ala Phe Arg Val Phe Asp Lys Asp Gly
            100                 105                 110

Asn Gly Tyr Ile Ser Ala Ala Glu Leu Arg His Val Met Thr Asn Leu
        115                 120                 125

Gly Glu Lys Leu Thr Asp Glu Glu Val Asp Glu Met Ile Arg Glu Ala
130                 135                 140

Asp Ile Asp Gly Asp Gly Gln Val Asn Tyr Glu Glu Phe Val Gln Met
145                 150                 155                 160
```

```
Met Thr Ala Lys Ser Thr Pro Cys Asp Asn Ala Met His Ser Ile Thr
                165                 170                 175

Glu Lys Pro Asn
            180

<210> SEQ ID NO 7
<211> LENGTH: 13
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 7

Pro Gly Arg Lys Lys Arg Arg Gln Arg Arg Pro Pro Gln
1               5                   10

<210> SEQ ID NO 8
<211> LENGTH: 16
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 8

Arg Gln Ile Lys Ile Trp Phe Gln Asn Arg Arg Met Lys Trp Lys Lys
1               5                   10                  15

<210> SEQ ID NO 9
<211> LENGTH: 27
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 9

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 10
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 10

Phe Arg Glu Lys Leu Ala Tyr Ile Ala Pro
1               5                   10

<210> SEQ ID NO 11
<211> LENGTH: 34
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 11

Asp Ala Ala Thr Ala Thr Arg Gly Arg Ser Ala Ala Ser Arg Pro Thr
1               5                   10                  15
```

Glu Arg Pro Arg Ala Pro Ala Arg Ser Ala Ser Arg Pro Arg Arg Pro
            20                  25                  30

Val Asp

<210> SEQ ID NO 12
<211> LENGTH: 27
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 12

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 13
<211> LENGTH: 21
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 13

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 14
<211> LENGTH: 12
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 14

Lys Ala Leu Ala Lys Ala Leu Ala Lys Ala Leu Ala
1               5                   10

<210> SEQ ID NO 15
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 15

Val Arg Leu Pro Pro Pro Val Arg Leu Pro Pro Pro Val Arg Leu Pro
1               5                   10                  15

Pro Pro

<210> SEQ ID NO 16
<211> LENGTH: 20
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 16

Gly Leu Phe Arg Ala Leu Leu Arg Leu Leu Arg Ser Leu Trp Arg Leu
1               5                   10                  15

Leu Leu Arg Ala
            20

<210> SEQ ID NO 17
<211> LENGTH: 8
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 17

Arg Arg Arg Arg Arg Arg Arg Arg
1               5

<210> SEQ ID NO 18
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 18

Arg Arg Arg Arg Arg Arg Arg Arg Arg
1               5

<210> SEQ ID NO 19
<211> LENGTH: 22
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 19

Leu Gly Thr Tyr Thr Gln Asp Phe Asn Lys Thr Phe Pro Gln Thr Ala
1               5                   10                  15

Ile Gly Val Gly Ala Pro
            20

<210> SEQ ID NO 20
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 20

Arg Gly Gly Arg Leu Ser Tyr Ser Arg Arg Arg Phe Ser Thr Ser Thr
1               5                   10                  15

Gly Arg

<210> SEQ ID NO 21
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 21

```
<210> SEQ ID NO 22
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 22

Tyr Gly Arg Lys Lys Arg Arg Gln Arg Arg Arg
1               5                   10

<210> SEQ ID NO 23
<211> LENGTH: 186
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 23

Met Gly His His His His His His His His Ser Ser Gly His Ile
1               5                   10                  15

Asp Asp Asp Asp Lys His Met Tyr Gly Arg Lys Lys Arg Arg Gln Arg
                20                  25                  30

Arg Arg Gly Gly Arg Met Ala Asp Gln Leu Thr Glu Glu Gln Ile Ala
            35                  40                  45

Glu Phe Lys Glu Ala Phe Ser Leu Phe Asp Lys Asp Gly Asp Gly Thr
    50                  55                  60

Ile Thr Thr Lys Glu Leu Gly Thr Val Met Arg Ser Leu Gly Gln Asn
65                  70                  75                  80

Pro Thr Glu Ala Glu Leu Gln Asp Met Ile Asn Glu Val Asp Ala Asp
                85                  90                  95

Gly Asn Gly Thr Ile Asp Phe Pro Glu Phe Leu Thr Met Met Ala Arg
            100                 105                 110

Lys Met Lys Asp Thr Asp Ser Glu Glu Glu Ile Arg Glu Ala Phe Arg
        115                 120                 125

Val Phe Asp Lys Asp Gly Asn Gly Tyr Ile Ser Ala Ala Glu Leu Arg
    130                 135                 140

His Val Thr Thr Asn Leu Gly Glu Lys Leu Thr Asp Glu Glu Val Asp
145                 150                 155                 160

Glu Met Ile Arg Glu Ala Asp Ile Asp Gly Asp Gly Gln Val Asn Tyr
                165                 170                 175

Glu Glu Phe Val Gln Met Met Thr Ala Lys
            180                 185
```

CELL PENETRATING PROTEIN ADAPTOR MOLECULES AND THEIR APPLICATION IN RESEARCH AND MEDICINE

Applicants incorporate by reference the material contained in the accompanying computer readable Sequence Listing identified as 077875_47_ST25.txt, having a file creation date of May 3, 2017 10:58 A.M. and file size of 16 kilobytes.

BRIEF DESCRIPTION OF FIGURES

The patent or application file contains at least two color figures. Copies of this patent or patent application publication with color drawing(s) will be provided upon request and payment of the necessary fee.

FIGS. 1-A-1-D show a scheme for the uptake of payloads tagged with a cell penetrating peptide (CPP) by cells. FIG. 1-A shows CPP tagged payload (3) is in medium outside cell membrane (2); internal compartments include nuclei, mitochondria, and endoplasmic reticulum. FIG. 1-B shows CPP tagged payload binds to specific sites on the cell membrane. FIG. 1-C shows binding induces invagination promoted uptake machinery in membrane. FIG. 1-D shows payload distributed in endosomes formed by invagination, cytoplasm, and internal compartments.

FIGS. 2-A-2-D show a scheme for the adaptor mediated uptake of payload by cells; association can be mediated by protein-protein or protein-ligand interactions. FIG. 2-A shows the association mediated by protein-protein or protein-ligand interactions of CPP tagged adaptor and cargo with adaptor ligand into binary complex. FIG. 2-B shows binding of binary complex to the cell membrane. FIG. 2-C shows internalization. FIG. 2-D shows dissociation and redistribution to internal compartments.

FIGS. 4-A-4-B show ribbon representations of the three dimensional structure of calmodulin, used here as an adaptor. FIG. 4-A shows the structure of $Ca^{2+}$-CaM bound to a canonical target peptide in the center of the molecule and FIG. 4-B shows the structure in the dumbbell-shaped conformation in the absence of target. The central helix breaks during recognition and binding, allowing calmodulin to wrap around the target. $Ca^{2+}$ are shown as small speres; the protein is less ordered in the absence of $Ca^{2+}$ (not shown). Free N and C termini are visible.

FIG. 5 shows amino acid sequence alignments of human calmodulin 1 (CALM) (SEQ ID NO: 1) and four 'calmodulin-like proteins:' TNNC2 (SEQ ID NO: 2), CETN1 (SEQ ID NO: 3), CALL5 (SEQ ID NO: 5), and CALL4 (SEQ ID NO: 4).

FIG. 6 shows the amino acid sequence of the synthetic CPP adaptor protein TAT-CaM, a CPP tagged calmodulin (corresponding to SEQ ID NO: 23). The short CPP binding sequence (TAT; SEQ ID NO: 22) is located directly before the NOTI site, which is followed by CaM (SEQ ID NO: 1).

FIGS. 7-A-7-B show confocal microscopy images demonstrating uptake of a fluorescence labeled enzyme (neuronal nitric oxide synthase (nNOS)) mediated by a CPP linked calmodulin adaptor 3 hours after uptake by BHO cells. Nucleus is stained blue; labeled nNOS is stained yellow with DiLight 540. FIG. 7-A shows nNOS added without CPP adaptor. Background still shows stained nNOS after washing with media. Some nNOS adheres to the cell surface; 3D cross sections show no nNOS inside cells. FIG. 7-B shows nNOS in the presence of TAT-CaM. A huge amount of nNOS is rapidly and actively pumped inside the cell, clearing the intracellular space and protecting nNOS from removal by washing. Cell boundary is now visible because the cytoplasm is stained by released nNOS. 3D cross sections confirm that labeled nNOS is inside the cells. Yellow circles inside the cells are labeled endosomes.

Figure 3:
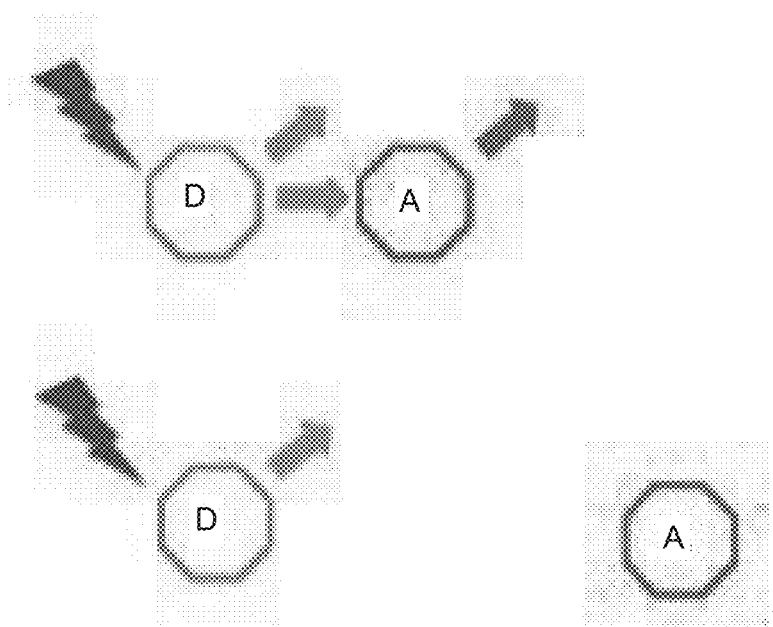
FIG. 3 shows the basic FRET (fluorescence resonance energy transfer) experiment to detect protein-protein interactions.

Proteins tagged with a variety of cell penetrating peptides (CPPs) have been used to manipulate the interior of cells in culture and in situ for more than a decade (1-19). Our innovation is the use of, coupling proteins that make strong protein-protein interactions to provide a convenient and powerful method to perturb cell interiors with a broad palette of selectively membrane permeable probes. Common and cheaply produced coupling proteins can be modified by introducing a CPP tag, enabling any protein that it binds to be moved into cells. It is relatively easy (and safe) to express and purify proteins with a tag that binds to a coupling protein with high affinity. Some tags allow rapid purification of the protein chosen for delivery using a one-step affinity column.

Delivery of proteins to the interior of cells has many applications. In addition to mapping the location of the components of living cells with fluorescent tags, the availability of a system capable of translocating proteins into the cell interior can enable detection of internal components in real time in living cells, and provide tools for the manipulation of signaling pathways and gene expression by allowing the introduction of constitutively active kinases, repressors, and enhancers. Virus detection and destruction inside cells is a long term possibility, as are medical applications based on altering the metabolic state and/or expression profiles of cells.

Cell Penetrating Peptides.

Over the last decade a number of peptides have been discovered or designed that are rapidly internalized by mammalian cells. Cell-penetrating peptides (CPPs) are capable of mediating penetration of the plasma membrane, allowing the delivery of macromolecular cargoes to the interior of cells (1, 2, 3). CPPs are typically 10 to 30 amino acids long. The three major categories are arginine-rich, amphipathic and lysine-rich, and hydrophobic (4). CPPs have been attached to the N and C termini of payload proteins, and to intermediate positions using a variety of chemical conjugation strategies (e.g., targeting cysteine thiols).

While the uptake of CPPs by cells is well established, the mechanism is somewhat controversial, and several pathways appear to be in use (5). In part, this reflects differences among the peptides, but there are indications that the same peptide may be taken up by different pathways under different circumstances. The initial interaction of CPP-protein constructs with cellular membranes is through interactions with hydrophobic components and/or negatively charged groups (phospholipids, heparin sulfate proteoglycans) on the membrane surface (see FIG. 1). Uptake of CPP bound payloads proceeds via binding to membrane and invagination. Depending on CPP tag, payloads can be targeted to internal compartments (nuclei, mitochondria) or cytoplasm. FIG. 1-A shows CPP tagged payload (3) is in medium outside cell membrane (2); internal compartments include nuclei, mitochondria, and endoplasmic reticulum. FIG. 1-B shows CPP tagged payload binds to specific sites on the cell membrane. FIG. 1-C shows binding induces invagination promoted uptake machinery in membrane. FIG. 1-D shows payload distributed in endosomes formed by invagination, cytoplasm, and internal compartments. The membrane associated, but not yet translocated, constructs are difficult to distinguish from translocated groups except by advanced 3D methods (e.g., confocal microscopy), which has led to artifacts in the study of CPP mechanisms. Once associated with the membrane surface, several translocation mechanisms can come into play (6). Evidence for clathrin dependent endocytosis, caveolin dependent endocytosis, and macropinocytosis has been presented for different combinations of CPP and cargo molecule, e.g., protein, nucleic acid, drug (5-8).

Since the initial discovery of the TAT peptide (TaTp) in 1988 (6), a variety of CPPs have been found to enable the transport of macromolecular cargoes to cells in culture and within living animals (1, 2, 3). A number of well characterized CPPs originated from the N or C termini of viral proteins; these include TATp, oligoarginines (6, 8), MPG peptides, Pep1 (9, 10) and VP22(11). The TAT CPP derived from the carboxy terminus of the dopamine transporter is capable of enabling the translocation of large cargoes, and synthetic CPPs such as Xentry (12) (a short (LCLRPVG) peptide based on the N terminal region of Hepatitis B X protein) are capable of carrying very large proteins across cell membranes.

An example is the 1,024 amino acid of *E. coli* 3-galactosidase, which exists as a 464-kDa homotetramer. Each unit of p-galactosidase subunit is a modular protein of five domains. These include a jelly-roll type barrel, two fibronectin type III-type barrels, a 0-sandwich domain, and a TIM-type barrel domain that contains the catalytic site. The ability of the CPP tag to enable translocation of an enormous multimer of modular components indicates that versatile translocation systems can be designed that use CPP tags to produce novel systems to manipulate the interior of cells.

Representative CPPs

| Peptides | Origin | Sequences | Cargo types |
|---|---|---|---|
| *Lysine rich CPPs and others derived from translocation domains* | | | |
| Tat | HIV-Tat protein | PGRKKRRQRRPPQ (SEQ ID NO: 7) | Protein/peptide/siRNA! liposome/nanoparticle |
| Penetratin | Homeodomain | RQIKIWFQNRRMKWKK (SEQ ID NO: 8) | peptide/siRNA/liposome |
| Transportan | Galanin-mastoparan | GWTLNSAGYLLGKINLKALAALAKKIL (SEQ ID NO: 9) | Protein/peptide/siRNA |
| Dat | Dopamine transporter | FREKLAYIAP (SEQ ID NO: 10) | Protein/peptide/siRNA |
| VP-22 | HSV-1 structural protein | DAATATRGRSAASRPTERPRAPAR-SASRPRRPVD (SEQ ID NO: 11) | Protein |
| *Amphipathic peptides* | | | |
| MPG | HIV Gp41-SV40 | GALFLGFLGAAGSTMGAWSQPKKKRKV (SEQ ID NO: 12) | siRNA/ODN/plasmid |
| Pep-1 | Trp-rich motif-SV40 NLS | KETWWETVWWTEWSQPKKKRKV (SEQ ID NO: 13) | Protein/peptide |
| MAP | Chimeric | KALAKALAKALA (SEQ ID NO: 14) | Small molecule/plasmid |
| SAP | Proline-rich motif | VRLPPPVRLPPPVRLPPP (SEQ ID NO: 15) | protein/peptide |
| PPTG1 | Chimeric | GLFRALLRLLRSLWRLLLRA (SEQ ID NO: 16) | Plasmid |
| *Arginine rich and other cell-penetrating peptides* | | | |
| Oligoarginine | Chimeric | Agr8 or Arg9 (SEQ ID NO: 17 and SEQ ID NO: 18, respectively) | Protein/peptide/siRNA/ODN |
| hCT (9-32) | Human calcitonin | LGTYTQDFNKTFPQTAIGVGAP (SEQ ID NO: 19) | Protein/plasmid DNA |
| SynB | Protegrin | RGGRLSYSRRRFSTSTGR (SEQ ID NO: 20) | Doxorubicin |
| Pvec | Murine VE-cadherin | LLIILRRRIRKQAHAHSK (SEQ ID NO: 21) | Protein/peptide |

CPP, cell-penetrating peptide; NLS, nuclear localization sequence; PNA, peptide-nucleic acid; Tat, transcription-transactivating. See refs (1-19).

CPP Tagged Adaptor Proteins.

The inventor here discloses the production of CPP tagged adaptor proteins capable of interacting with a wide variety of payloads. Adaptors are ideally small, stable and easily purified proteins capable of interacting strongly with the payload, either via intrinsic protein-protein interactions or via a ligand (e.g., a covalently attached group such as biotin). This strategy has several advantages. It provides a unified strategy that allows a payload protein to be purified by affinity chromatography using an N or C terminal extension, and the same extension can be used to mediated binding to the CPP tagged adaptor/carrier.

The strategy allows the production of payloads with only a single tag, rather than a CPP tag and an affinity tag. It also means that only a few CPP tagged adaptors need to be developed to deliver many different payloads. This is significant because the CPP tagged versions of many potential payloads carry a potential risk to workers involved in their purification due to the cell membrane permeability enhancement. Production of a limited number of relatively benign adaptor proteins under well-controlled conditions provides a significant safety factor, and the adaptor-payload complex need only be assembled at the point of use, in cases where complex formation is much faster than uptake by cells even being added separately to cell cultures.

The adaptor-payload complex can be designed to dissociate on internalization (see FIG. 2). One convenient way of doing this is to use an adaptor that responds to the internal cellular conditions, although other methods (an unstable linkage, autocatalytic dissociation, photodissociation) are also possible. The use of calcium by mammalian cells as a signal provides a promising avenue for release of payloads; cell interiors are normally maintained at very low levels of calcium by ATP driven pumps, and cells contain a variety of calcium biosensors that respond to transient increases in calcium to tightly bind and release target peptides. In a preferred embodiment, the adaptor protein is a calcium biosensor such as calmodulin. FIG. 2-A shows the association mediated by protein-protein or protein-ligand interactions of CPP tagged adaptor and cargo with adaptor ligand into binary complex. FIG. 2-B shows binding of binary complex to the cell membrane. FIG. 2-C shows internalization. FIG. 2-D shows dissociation and redistribution to internal compartments.

CPP Calmodulin.

Calmodulin is a multifunctional calcium biosensor that folds into a dumbbell-shaped configuration in the presence of calcium (20, 21). The ends of the dumbbell each contain two calcium binding EF hands. The alpha helix that connected the two globular regions breaks and closes around targets containing a 17 amino acid canonical motif or one of several alternative target motifs. Binding of CaM to targets is high affinity (picomolar) and is typically diffusion limited. CaM is a major mediator of calcium signaling in mammalian cells, and is the archetypical member of the EF hand-calmodulin superfamily of calcium signaling proteins. Calmodulin is small (16.7 kDa), soluble, and remarkably heat resistant. It is easy to produce site directed mutants and chimeras with calmodulin. The production of novel calmodulin constructs has the potential to provide unique and valuable reagents for cell biology research.

TAT peptides are short signal sequences that mediate transport of proteins across the membranes of many cells. Although TAT peptides were initially believed to work by directly mediating transport across phospholipid bilayers, they can drive the uptake of large proteins that could not cross the membrane without an active uptake process. It now appears that TAT peptides attach to receptors on the membrane and cause internalization in coated pits (5, 15, 17). Several patents have been granted for constructs that can be internalized by processes that rely on recognition of short TAT peptides attached as C or N terminal fusions.

Since the peptides are covalently attached through the peptide backbone, cargo remains attached to the CPP in cell interior. In addition, cargo proteins must be purified as CPP adducts. This means that expression in eukaryotes is complicated by binding to import machinery via the CPPs, and handling of the material is complicated because many desirable products are rendered potentially hazardous by the CPP tag.

The invention greatly extends the usefulness of TAT peptide constructs (and related CPP constructs) by expressing TAT fusions of small proteins that strongly bind other proteins. The inventor has designed a TAT calmodulin which is readily taken up by cells in culture (initially CHO cells) and should be taken up by cells in whole organisms. TAT was used as the initial CPP tag as the initial tag because of prior success in producing TAT tagged proteins that are taken up by mammalian cells, but other CPP tagged calmodulins are in production.

Initially, TAT tagged calmodulin was produced exactly as purify His-tagged calmodulin using His tag and nickel column. TAT tagged calcium biosensors can be purified using a column decorated with peptides recognized by the biosensor. For calmodulin, this is a 17 amino acid canonical sequence bound with high affinity in the presence of calcium. This will allow us to make calmodulin without the His tag by affinity chromatography, binding to the column in the presence of calcium and eluting with the calcium ionophore EDTA.

In a preferred embodiment, the payload delivered by the CPP tagged adaptor is a modulator (activator or repressor) of transcription. In another preferred embodiment, the payload is a probe that measures a property of the cell interior (e.g., an oxidation monitor, NO sensors, pH sensor). In another preferred embodiment, the payload is a kinase, phosphatase or other enzyme, which may be modified to be constitutively active.

Other payloads, including liposomes and their contents, nucleic acids, inhibitors, and drugs can also be delivered by extension of the method (e.g. using DNA binding proteins with calmodulin binding N or C terminal extensions. In a preferred embodiment, the payload is a nucleic acid delivered using a DNA or RNA binding protein with an adaptor recognition tag. In another a preferred embodiment, the payload is a drug or other small molecule delivered using a protein or other scaffold that binds the small molecule and is equipped with an adaptor recognition tag.

Tagged GFP and Other Fluorescent Probes.

Green Fluorescent Protein (GFP) and its engineered variants are powerful tools for the labeling of cell interiors. GFP is typically expressed after transfection with the appropriate vector, but many cell types are resistant to transfection. In a preferred embodiment, the payload delivered is a fluorescent probe such as a GFP fusion containing a site that recognizes an internal target and a tag recognized by a CPP adaptor (e.g., a calmodulin binding peptide recognized by TAT-CaM). GFP can be relatively easily purified, useful fluorescent probes are not limited to GFP and its homologs. They are widely used in part because they can be expressed in mammalian cells after transfection with a shuttle vector, and spontaneously generate a fluorophore inside the cells. The ability to deliver external probes broadens the possibilities.

A wide variety of proteins can be labeled with commercially available custom fluorophores (e.g., the extensive series sold by Alexa) and introduce them into the interior compartments of cells with CPP tags. This allows investigators to follow the tagged proteins in the cell with confocal microscopy, but also to conduct more demanding experiments, including FRET (fluorescence resonance energy transfer) and fluorescence lifetime experiments (see FIG. 3). As shown in FIG. 3, excitation of D leads to emission from A only when A and D are in proximity due to complex formation. This also reduces emission from the donor. Examples of donor acceptor pairs with good overlap include Alexa Fluor 488 and Alexa Fluor 647.

In FRET experiments, components are labeled with fluorophores chosen so that the emission spectrum of one (the donor) is heavily overlapped with the excitation spectrum of the other (the acceptor). If the labeled molecules associate in the cell, Forster energy transfer will cause the acceptor to fluoresce when the donor is excited by pumping its absorbance lines. This provides information about complex formation in cells.

In lifetime experiments, a fluorophore is repeatedly excited by a pulse from a laser and the fluorescence decays are collected, yielding the lifetimes of the fluorophore in all environments. Typically three or four environments can be readily distinguished with lifetimes in the 50 ps to 5 ns range and contributions as low as a few percent.

FRET experiments can be carried out inside cells using two different GFP variants, but using CPP adaptors to deliver a pair of proteins labeled with different synthetic fluorophores would be advantageous for several reasons. Paired fluorophores optimized for FRET are sold by Alexa and DyLight. These have far better properties (e.g., yield and spectral overlap) than the engineered GFP variants. An important advantage is that they are small and introduce much less steric interference than a GFP fusion.

Calmodulin and the EF Hand Proteins.

Calmodulin is remarkable for its high sequence conservation; only four other proteins are more conserved in eukaryotes. Mammalian calmodulins are identical, and the *C. elegans* protein is 96% identical to its human homolog. The sequence homology of calmodulin is not imposed primarily by the requirement for calcium binding and the associated organization into the characteristic dumbbell shape (FIG. 4); this could be accomplished by far lower levels of similarity. Instead, the primary driver of conservation is the retention of target specificity. Since calmodulin binds to many $Ca^{2+}$ activated targets in cells, the ability of the targets and calmodulin to co-evolve is severely restricted. FIG. 4-A shows the structure of $Ca^{2+}$-CaM bound to a canonical target peptide in the center of the molecule and FIG. 4-B shows the structure in the dumbbell-shaped conformation in the absence of target. The central helix breaks during recognition and binding, allowing calmodulin to wrap around the target. $Ca^{2+}$ are shown as small speres; the protein is less ordered in the absence of $Ca^{2+}$ (not shown). Free N and C termini are visible.

As shown in the alignment of FIG. 5, sequence similarity within the calmodulin-EF hand superfamily is much lower; identity within the four human sequences shown is ~20%. The similarity of these human calmodulin homologs is much less than the similarity of human and *C. elegans* calmodulin; less than 2% of the positions are identically conserved. The sequence variation within the superfamily allows the members to recognize and regulate distinct targets in response to a single ionic signal. It allows us to make use of the different specificity of superfamily members to produce EF hand based adaptors that are specific to different target sequences (22, 23); all these targets are roughly 17 AA in length because of the dimensions of the folded EF hand proteins, but the amino acid sequences of the targets are different. (There are different binding modes for some targets, but this is not important for our purposes). This is important in the long run because it confers potential to address different payloads to different cellular compartments (10).

Structures of calcium-calmodulin bound to a canonical target peptide (left) and in the dumbbell-shaped conformation in the absence of target (right). The central helix breaks during recognition and binding, allowing calmodulin to wrap around the target. The protein is less ordered in the absence of calcium (not shown).

Delivery of Payloads with CPP Tagged Calmodulin

Good evidence has been obtained for delivery of target proteins to the interior of cells with CPP labeled calmodulin. The initial demonstrations were designed to use neuronal nitric oxide synthase (24) and CaM Kinase (25); both enzymes are activated by calcium/calmodulin, and both can be purified on a calmodulin column. CaM kinase isoforms have monomer molecular masses of ~41 kDa; the truncated CaM kinase II sold by New England Biolabs has a molecular mass of 36 kDa. However, CaM kinases form very large quartenary complexes of 400-600 kDa, making them an exacting test for the calmodulin mediated translocation system, comparable to beta-galactosidase. The nNOS active dimer has a molecular mass of ~322 kDa. Both proteins can be readily labeled with high quantum yield fluorophores that have distinctive spectral signatures, allowing their uptake and cellular distribution to be readily evaluated.

These proteins were chosen because they contain a calmodulin binding motif, but most proteins can be produced with a small calmodulin binding tag at the N or C terminus without significantly affecting their activity, or like neuronal nitric oxide synthase (nNOS) with an internal tag associated with an exposed surface loop.

An obvious alternative is the attachment of a CPP directly to the payload. Numerous patents cover the use of various CPPs attached to payloads by covalent or in a few cases non-specific non-covalent interactions. There are several drawbacks: this requires additional handing of potentially toxic CPPs, and the CPP would remain on the tag after internalization.

In one embodiment of the current invention, payloads are tagged with an adaptor recognized moiety (e.g., a calmodulin binding peptide) using standard cross linking methods (see FIG. 7). FIG. 7-A shows nNOS added without CPP adaptor. Background still shows stained nNOS after washing with media. Some nNOS adheres to the cell surface; 3D cross sections show no nNOS inside cells. FIG. 7-B shows nNOS in the presence of TAT-CaM. A huge amount of nNOS is rapidly and actively pumped inside the cell, clearing the intracellular space and protecting nNOS from removal by washing. Cell boundary is now visible because the cytoplasm is stained by released nNOS. 3D cross sections confirm that labeled nNOS is inside the cells. Yellow circles inside the cells are labeled endosomes. For proteins that are produced by investigators themselves, it removes the advantages of integrated affinity purification and CPP-adaptor attachment. Nevertheless, for some applications the direct coupling approach could prove to be a useful alternative. For example, commercially obtained proteins with no CaM binding site can readily be tagged and rendered cell permeable this way.

The embodiments shown and described in the specification are only specific embodiments of inventor who is skilled in the art and are not limiting in any way. Therefore, various changes, modifications, or alterations to those embodiments may be made without departing from the spirit of the invention in the scope of the following claims. The references cited are expressly incorporated by reference herein in their entirety.

REFERENCED BY

| Citing Patent | Filing date | Publication date | Applicant | Title |
| --- | --- | --- | --- | --- |
| U.S. Pat. No. 7,034,109* | Oct. 15, 2001 | Apr. 25, 2006 | Christophe Bonny | Intracellular delivery of biological effectors |

-continued

| Citing Patent | Filing date | Publication date | Applicant | Title |
|---|---|---|---|---|
| U.S. Pat. No. 7,538,091 | Apr. 21, 2006 | May 26, 2009 | Xigen, S. A. | D-retro-inverso amino acid sequence transporter peptide conjugated to nucleic acid biological effector; translocation across the membrane of pancreatic B-cells |
| U.S. Pat. No. 7,569,674 | Apr. 29, 2005 | Aug. 4, 2009 | Innexus Biotechnology International Limited | Autophilic antibodies |
| U.S. Pat. No. 7,662,178 | Apr. 29, 2008 | Feb. 16, 2010 | The Trustees Of Columbia University In The City Of New York | C3 exoenzyme-coated stents and uses thereof for treating and preventing restenosis |
| U.S. Pat. No. 7,727,958 | Sep. 4, 2007 | Jun. 1, 2010 | Kai Pharmaceuticals, Inc. | Pharmaceutical formulation |
| U.S. Pat. No. 7,754,678 | Oct. 17, 2005 | Jul. 13, 2010 | Aventis Pharmaceuticals, Inc. | Membrane penetrating peptides and uses thereof |
| U.S. Pat. No. 7,927,580 | Mar. 16, 2005 | Apr. 19, 2011 | Nanirx, Inc. | Identifying new immunomodulatory chemical entities (NICE); reacting a candidate NICE with a Tat SH3 binding domain, identifying the bound candidate NICE and determining whether it induces monocytes to differentiate into dendritic cells (DC) or regulatory macrophages (AReg); drug screening; immunotherapy |
| U.S. Pat. No. 8,067,532 | Jan. 22, 2008 | Nov. 29, 2011. | Kai Pharmaceuticals, Inc. | Modifications of peptide compositions to increase stability and delivery efficiency |
| U.S. Pat. No. 8,080,517 | Sep. 12, 2005 | Dec. 20, 2011 | Xigen Sa | Cell-permeable peptide inhibitors of the JNK signal transduction pathway |
| U.S. Pat. No. 8,183,339 | Oct. 12, 2000 | May 22, 2012 | Xigen S. A. | Cell-permeable peptide inhibitors of the JNK signal transduction pathway |
| U.S. Pat. No. 8,236,924 | Apr. 11, 2008 | Aug. 7, 2012 | Xigen Sa | Cell-permeable peptide inhibitors of the JNK signal transduction pathway |
| U.S. Pat. No. 8,273,867 | Feb. 9, 2007 | Sep. 25, 2012 | The Regents Of The University Of California | Transducible delivery of siRNA by dsRNA binding domain fusions to PTD/CPPS |

-continued

REFERENCED BY

| Citing Patent | Filing date | Publication date | Applicant | Title |
|---|---|---|---|---|
| U.S. Pat. No. 8,278,413 | Aug. 31, 2011 | Oct. 2, 2012 | Xigen Sa | Cell-permeable peptide inhibitors of the JNK signal, transduction pathway |
| U.S. Pat. No. 8,524,673 | Apr. 21, 2010 | Sep. 3, 2013 | Pharmaceuticals, Inc. | Pharmaceutical formulation |
| U.S. Pat. No. 8,569,447 | Jul. 20, 2012 | Oct. 29, 2013 | Xigen Sa | Cell-permeable peptide inhibitors of the JNK signal transduction pathway |
| U.S. Pat. No. 8,748,395 | Sep. 12, 2006 | Jun. 10, 2014 | Xigen Inflammation Ltd. | Cell-permeable peptide inhibitors of the JNK signal transduction pathway |
| EP1544305A1 * | Dec. 18, 2003 | Jun. 22, 2005 | Medizinische Hochschule Hannover | Adapter for docking a substance to the cell wall |
| EP1605893A2 * | Mar. 5, 2004 | Dec. 21, 2005 | Immpheron Incorporated | Trans-membrane-antibody induced inhibition of apoptosis |
| EP1964853A1 * | Feb. 27, 2008 | Sep. 3, 2008 | NTT DoCoMo, Inc. | Methods of synthesizing and preserving a nucleotide-labeled microtubule |
| WO2003077931 AI * | Mar. 17, 2003 | Sep. 25, 2003 | Findeis Mark A | Transcription factor modulators and uses thereof |
| WO2004030610 A2 * | Jul. 11, 2003 | Apr. 15, 2004 | Univ Columbia | Compositions and methods for the intracellular delivery of antibodies |
| WO2004064780 A2 * | Jan. 13, 2004 | Aug. 5, 2004 | Cheresh David A | Peptide-based angiogenesis inhibitors and methods of use thereof |
| US 20110027300 AI | Feb. 13, 2009 | Feb. 3, 2011 | Max-Planck-Gesellschaft Zur Forderung Der Wissenschaften E. V. | Identification of a novel cysteine-rich cell penetrating peptide |
| U.S. Pat. No. 6,316,003 B1 | Apr. 28, 1994 | Nov. 13, 2001 | Whitehead Institute | Presenting to the cell an extracellular fusion protein consisting of a cargo moiety and a transport moiety and allowing transport moiety-dependent intracellular delivery of the fusion protein |
| WO2005059129A2* | Dec. 17, 2004 | Jun. 30, 2005 | Hannover Med Hochschule | Adapter for coupling a substance which is to be coupled to a cell surface |

What is claimed is:

1. A complex for translocating a cargo into a cell interior, the complex comprising a cell penetrating peptide (CPP) fused to an adapter and the cargo, wherein the cargo comprises an adapter binding molecule, wherein the adapter binding molecule reversibly binds to the adapter, and wherein the adaptor is calmodulin and the adaptor binding molecule is a calmodulin binding peptide.

2. The complex of claim 1, wherein the cell penetrating peptide is TAT.

3. The complex of claim 1 comprising SEQ ID NO: 22 and SEQ ID NO: 1.

4. The complex of claim 1, wherein the cargo is selected from the group consisting of a modulator of transcription, probe, enzyme, liposome, nucleic acids, inhibitor, fluorescent probe, small molecule, and drug.

5. A method for delivering a cargo into a cell, the method comprising:

contacting the cell with a biological complex under conditions suitable for translocating the biological complex into the cell, the biological complex comprising a cell penetrating peptide fused to an adaptor and the cargo, wherein the cargo comprises an adapter binding molecule, and wherein the adaptor is calmodulin and the adaptor binding molecule is a calmodulin binding peptide; and translocating the complex into the cell interior to deliver the cargo into the cell interior.

6. The method of claim 5, wherein the cell penetrating peptide is TAT.

7. The method of claim 5, wherein the complex comprises SEQ ID NO: 22 and SEQ ID NO: 1.

8. The method of claim 5, wherein the cargo is selected from the group consisting of a modulator of transcription, probe, enzyme, liposome, nucleic acids, inhibitor, fluorescent probe, small molecule, and drug.

9. The method of claim 5, wherein the cargo is used for internal measurements of cell conditions.

10. The method of claim 5, wherein the cargo is delivered to internal cell compartments to detect or measure the presence of targets.

11. The method of claim 5, wherein the cargo perturbs the state of cells, modifies expression, modifies the genome of an organism, or treats a disease.

12. The method of claim 5, wherein the cargo is expressed with a calmodulin binding peptide as the adaptor binding molecule as an N or C terminal extension and purified on a calmodulin affinity column.

* * * * *